United States Patent [19]
Rosen et al.

[11] Patent Number: 5,504,223
[45] Date of Patent: Apr. 2, 1996

[54] SYNTHESIS OF CYCLOPENTADIENYL METAL COORDINATION COMPLEXES FROM METAL HYDROCARBYLOXIDES

[75] Inventors: Robert K. Rosen, Sugar Land; Brian W. S. Kolthammer, Lake Jackson, both of Tex.

[73] Assignee: The Dow Chemical Company, Midland, Mich.

[21] Appl. No.: 186,402

[22] Filed: Jan. 25, 1994

[51] Int. Cl.⁶ .............................. C07F 7/00; C07F 17/00
[52] U.S. Cl. .................. 556/7; 556/11; 556/12; 556/20; 556/22; 556/28; 556/53; 556/54; 556/56
[58] Field of Search .................... 556/7, 11, 12, 556/20, 22, 28, 53, 54, 56

[56] References Cited

U.S. PATENT DOCUMENTS

| | | | |
|---|---|---|---|
| 5,026,798 | 6/1991 | Canich | 526/127 |
| 5,064,802 | 11/1991 | Stevens et al. | 502/155 |
| 5,158,920 | 10/1992 | Razavi | 502/152 |

FOREIGN PATENT DOCUMENTS

| | | |
|---|---|---|
| 0416815 | 3/1991 | European Pat. Off. . |
| 0468651 | 1/1992 | European Pat. Off. . |
| 0514828 | 11/1992 | European Pat. Off. . |
| 0530908 | 3/1993 | European Pat. Off. . |
| 04072309 | 3/1992 | Japan . |
| WO9200333 | 1/1992 | WIPO . |
| WO9210360 | 12/1992 | WIPO . |

OTHER PUBLICATIONS

Chem. Ber 123, (1990) 1649–1651.
Chem. Ber 119, (1986) 1750–1754.
J. of Organometallic Chemistry 369, (1989) 359–370.

*Primary Examiner*—Porfirio Nazario-Gonzalez

[57] ABSTRACT

A process for preparing bridged mono- and bis(cyclopentadienyl) metal dihydrocarbyloxy coordination complexes (I) by contacting in the presence of an aprotic organic diluent a metal compound of the formula $M(OR)_4$ with a dianionic salt compound. A process for preparing bridged mono- and bis(cyclopentadienyl)dihydrocarbyl metal coordination complexes (II) by contacting a complex (I) with a hydrocarbylation agent. A process for preparing bridged mono- and bis(cyclopentadienyl) metal dihalide coordination complexes (III) by contacting a complex (I) with a halogenation agent.

10 Claims, No Drawings

SYNTHESIS OF CYCLOPENTADIENYL METAL COORDINATION COMPLEXES FROM METAL HYDROCARBYLOXIDES

BACKGROUND OF THE INVENTION

The present invention relates to a process for preparing certain bridged mono- and bis-cyclopentadienyl metal dihydrocarbyloxy coordination complexes starting from metal hydrocarbyloxide compounds. The present invention also relates to a process for preparing bridged mono- and bis-cyclopentadienyl dihydrocarbyl metal coordination complexes and to a process for preparing bridged mono- and bis-cyclopentadienyl metal dihalide coordination complexes both starting from the corresponding bridged mono- or bis-cyclopentadienyl metal dihydrocarbyloxy coordination complexes.

Bridged mono- and bis-cyclopentadienyl metal dihalide coordination complexes and bridged mono- and bis-cyclopentadienyl dihydrocarbyl metal coordination complexes are known and useful as addition polymerization catalysts or as components or precursors thereof.

In "Metallkomplexe mit verbrueckten permethylierten Cyclopentadienylliganden" of P. Jutzi and R. Dickbreder, Chem. Ber. 119, 1750–1754 (1986) the synthesis is described of dimethylsilanediyl-bridged bis(permethylated cyclopentadienyl) titanium dichlorides from the tetrahydrofuran (THF) adducts of titanium tetrachloride and the dimethylsilanediyl-bridged bis(permethylated cyclopentadienyl) dianion derivatives.

In "ansa-Metallocene derivatives: XVII. Racemic and meso diastereoisomers of group IV metallocene derivatives with symmetrically substituted, dimethylsilanediyl-bridged ligand frameworks. Crystal structure of R,S—Me$_2$Si(3—t—Bu—MeC$_5$H$_2$)$_2$ZrCl$_2$" of H. Wiesenfeldt et al., Journal of Organometallic Chemistry, 369 (1989)359–370 the synthesis is described of dimethylsilanediyl-bridged bis(substituted cyclopentadienyl) titanium dichloride complexes from the THF-adducts of titanium trichoride and the dimethylsilanediyl-bridged bis(substituted cyclopentadienyl) dianion derivatives.

In "Synthesis and Complexation of Linked Cyclopentadienyl-Amido Ligands" of J. Okuda, Chem. Ber. 123 (1990) 1649–1651 the preparation is described of a bridged mono-(substituted cyclopentadienyl) titanium dichloride complex from the THF-adduct of titanium tetrachloride and the dilithium salt of [(tertbutylamino)dimethylsilyl] (tert-butyl) cyclopentadienide.

Bridged mono-cyclopentadienyl metal dihalide coordination complexes are also prepared in U.S. Pat. No. 5,026,798 from titanium tetrachloride compounds or ether adducts thereof and the dilithium salts of bridged mono-cyclopentadienyl ligand compounds.

Further, EP-A-0,416,815 teaches a process to prepare bridged mono-cyclopentadienyl metal dihalide coordination complexes starting from the transition metal tetrahalide and a Group 1 or Grignard derivative of the bridged monocyclopentadienyl ligand compounds.

The above-mentioned synthesis methods to prepare the bridged mono- and bis-cyclopentadienyl metal dihalide coordination complexes use metal tetrahalide compounds as starting materials, which are corrosive, toxic, and air and moisture sensitive. In order to facilitate handling thereof, prior to the reaction step the transition metal tetrahalide compound is typically converted to its ether-adduct in a separate step with for example THF or diethyl ether. This adduct formation step in itself proceeds with difficulty, requiring low to very low temperatures, and an inert atmosphere. The adduct is usually recovered before it is reacted with the dianionic derivative of the ligand compound. The yield of the adduct formation step or steps is less than quantitative. Furthermore, the reaction mixture of the transition metal tetrahalide compound and the dianionic derivative of the bridged cyclopentadienyl ligand compound requires a multi-step, laborious recovery and purification procedure. Typically, after the reaction step, the solvent is removed, the product redissolved by adding dichloromethane or toluene or a mixture thereof, the metal halide byproduct, typically lithium chloride, removed by filtration of the mixture, the solvent removed at least partially, followed by redissolving the solid product and crystallizing the product, optionally followed by one or more further recrystallization procedures.

Further, it is known to from EP-A-0,416,815 and EP-A-0,514,828 to prepare bridged mono-cyclopentadienyl metal dihalide coordination complexes, by reacting the THF-adduct of a transition metal trihalide compound, especially TiCl$_3$, with the dianionic derivative of the cyclopentadienyl ligand. The resulting complex is contacted with a noninterfering oxidizing agent, such as for example AgCl (EP-A-0,416,815), or with an organic halide to raise the oxidation state of the metal to form the desired dihalide complex. Apart from requiring an extra reaction step, that is the oxidation step, this process also starts from the transition metal trihalide or an ether-adduct thereof which has the disadvantages listed above, and requires long reaction times to be prepared. Furthermore, the complex resulting from the reaction between the ether adduct of the transition metal trihalide compound with the dianionic derivative of the cyclopentadienyl ligand, i.e. the cyclopentadienyl metal(III) monohalide coordination complex, is thermally unstable.

The bridged mono-cyclopentadienyl dihydrocarbyl metal coordination complexes can be prepared by hydrocarbylating the corresponding bridged mono-cyclopentadienyl metal dihalide coordination complexes with a Grignard, lithium, sodium or potassium salt of the hydrocarbyl ligand. This is described, for example, in EP-A-0,418,044, example 3 and WO 92/00333. These preparation processes inherently have the disadvantages associated with the preparations of the bridged mono-cyclopentadienyl metal dihalide coordination complexes.

SUMMARY OF THE INVENTION

In one aspect, the present invention relates to a process for preparing a metal dihydrocarbyloxy coordination complex corresponding to the formula:

wherein:

M is titanium;

Cp* is a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Cp* to have a fused ring structure;

Z is a divalent moiety comprising boron, or a member of Group 14 of the Periodic Table of the Elements, and optionally sulfur or oxygen, said moiety having up to 50 non-hydrogen atoms, and optionally Cp* and Z together form a fused ring system;

Y is a) a divalent anionic ligand group comprising nitrogen, phosphorus, oxygen or sulfur and having up to 20 non-hydrogen atoms, said Y being bonded to Z and M through said nitrogen, phosphorus, oxygen or sulfur, and optionally Y and Z together form a fused ring system, or b) a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Y to have a fused ring structure; and R independently each occurrence is a hydrocarbyl group having from 1 to 20 carbon atoms; the steps of the process comprising:
contacting in the presence of an aprotic organic diluent a metal compound of the formula: $M(OR)_4$ wherein M and R are as previously defined with a dianionic salt compound corresponding to the formula:

$$(L^{+x})_{y(Cp^*-Z-Y)}^{-2} \text{ or } ((LX)^{+x})_y(Cp^*-Z-Y)^{-2}$$

wherein:
L is a metal of Group 1 or 2 of the Periodic Table of the Elements,
X independently is chloro, bromo, or iodo, x and y are either 1 or 2 and the product of x and y equals 2, and
Cp*, Z, and Y are as previously defined;
to form the complex of formula (I).

In another aspect, the present invention relates to a process for preparing a metal dihydrocarbyl coordination complex corresponding to the formula:

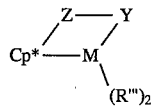  (II)

wherein:
M is titanium;

Cp* is a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Cp* to have a fused ring structure;

Z is a divalent moiety comprising boron, or a member of Group 14 of the Periodic Table of the Elements, and optionally sulfur or oxygen, said moiety having up to 50 non-hydrogen atoms, and optionally Cp* and Z together form a fused ring system;

Y is a) a divalent anionic ligand group comprising nitrogen, phosphorus, oxygen or sulfur and having up to 20 non-hydrogen atoms, said Y being bonded to Z and M through said nitrogen, phosphorus, oxygen or sulfur, and optionally Y and Z together form a fused ring system, or b) a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Y to have a fused ring structure; and R''' independently each occurrence is a hydrocarbyl group;

the process comprising contacting in the presence of an aprotic organic diluent a metal coordination complex of formula:

  (I)

wherein R independently each occurrence is a hydrocarbyl group having from 1 to 20 carbon atoms and Cp*, Z, Y, M, are as previously defined;

with a hydrocarbylation agent comprising a group 1, 2, 12 or 13 metal or metal derivative and at least one hydrocarbyl group R''', to form the metal dihydrocarbyl coordination complex of formula (II).

In yet another aspect the present invention relates to a process for preparing a metal dihalide coordination complex corresponding to the formula:

  (III)

wherein:
M is titanium, zirconium, or hafnium;

Cp* is a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Cp* to have a fused ring structure;

Z is a divalent moiety comprising boron, or a member of Group 14 of the Periodic Table of the Elements, and optionally sulfur or oxygen, said moiety having up to 50 non-hydrogen atoms, and optionally Cp* and Z together form a fused ring system;

Y is a) a divalent anionic ligand group comprising nitrogen, phosphorus, oxygen or sulfur and having up to 20 non-hydrogen atoms, said Y being bonded to Z and M through said nitrogen, phosphorus, oxygen or sulfur, and optionally Y and Z together form a fused ring system, or b) a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Y to have a fused ring structure; and X independently each occurrence is a halo group;

the process comprising contacting in the presence of an aprotic organic diluent a metal coordination complex of formula:

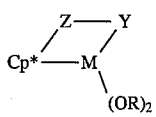

$$\begin{array}{c} Z\text{---}Y \\ Cp^*\text{---}M \\ \quad\quad (OR)_2 \end{array} \quad (I)$$

wherein R independently each occurrence is a hydrocarbyl group having from 1 to 20 carbon atoms and Cp*, Z, Y, M, are as previously defined;

with a halogenation agent comprising at least a member of Group 13 or 14 of the Periodic Table of the Elements and at least one halo group X, to form the metal dihalide coordination complex of formula (III).

DETAILED DESCRIPTION OF THE INVENTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering Groups.

Surprisingly, it has been found that two hydrocarbyloxy groups on the titanium center can be removed readily by contacting the compound M(OR)4 with the dianionic salt compound to give the complexes of formulas (I), (Ia), or (Ib) in high yield and high purity. This discovery was indeed surprising as hydrocarbyloxy-transition metal bonds are considered to be stronger bonds than halogen-transition metal bonds and therefore the hydrocarbyloxy groups are considered less suitable leaving groups than halogen groups. The starting metal hydrocarbyloxy compounds, typically the titanium tetraisopropoxide, tetra-n-butoxide and tetra-t.-butoxide, are non-viscous liquids, only mildly air-sensitive, commercially available, and readily soluble in hydrocarbons, as compared to the corrosive, air-sensitive and difficult to handle titanium tetrachlorides. This new process provides the complexes of formulas (I), (Ia), and (Ib) in yields of 90 percent and higher. The product complexes can be readily isolated in high purity by filtration.

In the present process bridged mono-or bis(cyclopentadienyl ) metal dihydrocarbyloxy coordination complexes of formulas (I), (Ia), or (Ib) are prepared by contacting a titanium tetrahydrocarbyloxy compound of the formula: $M(OR)_4$ with a dianionic salt compound. The dianionic salt is preferably a double Group 1 metal derivative or double Grignard (Group 2 metal monohalide) derivative of the —Cp*—Z—Y— moiety, the anionic charges formally residing on the Cp* and Y groups. The double Group 1 metal derivative corresponds to $(L^{+x})_y$ wherein x is 1 and y is 2, and the double Grignard derivative corresponds to $((LX)^{+x})_y$ wherein x is 1 and y is 2.

In the metal dihydrocarbyloxy coordination complexes of formula (I), M is titanium, and R independently each occurrence is a hydrocarbyl group having from 1 to 20 carbon atoms, more preferably R each occurrence is independently selected from the group consisting of alkyl, aryl, alkaryl, and aralkyl groups, even more preferably from alkyl groups having from 1 to 6 carbon atoms, and aryl, aralkyl and alkaryl groups having from 6–10 carbon atoms, and most preferably R each occurrence is independently selected from the group consisting of isopropyl, n-butyl, and t-butyl.

A neutral Lewis base, such as an ether or amine compound, may also be associated with the complex, if desired, however, such is generally not preferred.

The term "substituted cyclopentadienyl" includes indenyl, tetrahydroindenyl, fluorenyl, tetrahydrofluorenyl, and octahydrofluorenyl groups.

Generic formula (I) embraces bridged monocyclopentadienyl metal dihydrocarbyloxy coordination complexes and bridged bis(cyclopentadienyl) metal dihydrocarbyloxy coordination complexes.

Preferred bridged monocyclopentadienyl metal dihydrocarbyloxy coordination complexes of formula (I) prepared in the present process include those having constrained geometry.

By the term "constrained geometry" as used herein is meant that the metal atom in the metal coordination complex and also in the catalyst resulting therefrom is forced to greater exposure of the active catalyst site because of a specific ring structure of a ligand group including the metal atom, wherein the metal is both bonded to an adjacent covalent moiety and held in association with the delocalized $\pi$-bonded cyclopentadienyl group through an $\eta^5$ or other $\pi$-bonding interaction. It is understood that each respective bond between the metal atom and the constituent atoms of the $\pi$-bonded moiety need not be equivalent. That is, the metal may be symmetrically or unsymmetrically $\pi$-bound thereto.

The concept of constrained geometry and specific constrain inducing ligand groups are described in more detail in U.S. patent application Ser. No. 545,403, filed Jul. 3, 1990 (corresponding to EP-A-0,416,815) which is incorporated herein by reference.

Suitable examples of moiety Z in formula (I) include $SiR^*_2$, $CR^*_2$, $SiR^*_2SiR^*_2$, $CR^*_2CR^*_2$, $CR^*=CR^*$, $CR^*_2SiR^*_2$, $GeR^*2$, $BR^*$, or $BR^*2$ wherein R* each occurrence is independently selected from the group consisting of hydrogen, alkyl, aryl, silyl, halogenated alkyl, halogenated aryl groups having up to 20 non-hydrogen atoms, and mixtures thereof, or two or more R* groups from Z, or an R* group from Z together with Y form a fused ring system.

Further more preferably, Y in formula (I) is —O—, —S—, —NR*—, —PR*—. Highly preferably Y is a nitrogen or phosphorus containing group corresponding to the formula —N(R')— or —P(R')—, i.e. an amido or phosphido group, wherein R' is as defined hereinafter.

More preferably, in the present process is prepared a metal coordination dihydrocarbyloxy complex of formula (I) corresponding to the formula:

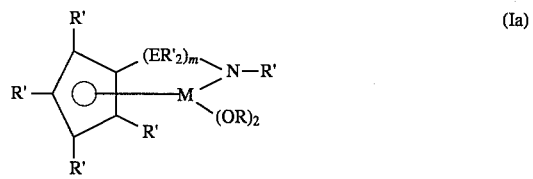

wherein R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;

m is 1 or 2; and

M and R are as previously defined; and wherein the metal compound of the formula: $M(OR)_4$ is contacted with a dianionic salt compound corresponding to the formula:

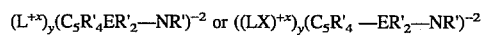

wherein L, R', E, X, x and are previous y as 1 defined.

In the complexes of formula (Ia), M is titanium, and preferably R independently each occurrence is alkyl, aryl, aralkyl, and alkaryl groups, more preferably selected from an alkyl group having from 1 to 6 carbon atoms, and aryl, aralkyl and alkaryl groups having from 6–10 carbon atoms, even more preferably R is isopropyl, n-butyl, or t-butyl.

Examples of the above most highly preferred metal dihydrocarbyloxy coordination compounds include compounds wherein the R' on the amido group is methyl, ethyl, propyl, butyl, pentyl, hexyl, and isomers of these alkyl radicals, norbornyl, benzyl, phenyl, etc.; the cyclopentadienyl group is cyclopentadienyl, indenyl, tetrahydroindenyl, fluorenyl, tetrahydrofluorenyl, octahydrofluorenyl, etc.; R' on the foregoing cyclopentadienyl groups each occurrence is hydrogen, methyl, ethyl, propyl, butyl, pentyl, hexyl, and isomers of these alkyl radicals, norbornyl, benzyl, phenyl, etc.; and R is isopropyl, n-butyl or t-butyl.

Specific highly preferred compounds include: (tert-butylamido)(tetramethyl-$\eta^5$-cyclopentadienyl)-1,2-ethanediyltitanium di-isopropoxide, (tert-butylamido)(tetramethyl-$\eta^5$-cyclopentadienyl)-1,2-ethanediyltitanium di-n-butoxide, (tert-butylamido)(tetramethyl-$\eta^5$-cyclopentadienyl)dimethylsilanetitanium di-isopropoxide, (tert-butylamido)(tetramethyl-$\eta^5$-cyclopentadienyl)dimethylsilanetitanium di-n-butoxide, (methylamido)(tetramethyl-$\eta^5$-cyclopentadienyl)dimethylsilanetitanium di-isopropoxide, (methylamido)(tetramethyl-$\eta^5$-cyclopentadienyl)dimethylsilanetitanium di-n-butoxide, (phenylamido)(tetramethyl-$\eta^5$-cyclopentadienyl)dimethylsilanetitanium diisopropoxide, (phenylamido)(tetramethyl-$\eta^5$-cyclopentadienyl)dimethylsilanetitanium di-n-butoxide, (benzylamido)(tetramethyl-$\eta^5$-cyclopentadienyl)dimethylsilanetitanium di-isopropoxide, (benzylamido)(tetramethyl-$\eta^5$-cyclopenta-dienyl)dimethylsilanetitanium di-n-butoxide, (tertbutylamido)($\eta^5$-cyclopentadienyl)-1,2-ethanediyltitanium di-isopropoxide, (tert-butylamido)($\eta^5$-cyclopentadienyl)-1,2-ethanediyltitanium di-n-butoxide, (tertbutylamido)($\eta^5$-cyclopentadienyl)dimethylsilanetitanium di-isopropoxide, (tert-butylamido)($\eta^5$-cyclopentadienyl)dimethylsilanetitanium di-n-butoxide, (methylamido)($\eta^5$-cyclopentadienyl)dimethylsilanetitanium di-isopropoxide, (t-butylamido)($\eta^5$-cyclopentadienyl)dimethylsilanetitanium di-n-butoxide, (t-butylamido)indenyldimethylsilanetitanium di-isopropoxide, (t-butylamido) indenyldimethylsilanetitanium di-n-butoxide, (benzylamido)indenyldimethylsilanetitanium diisopropoxide.

According to another preferred embodiment of the present process, there is prepared a metal coordination complex of formula (I) corresponding to the formula:

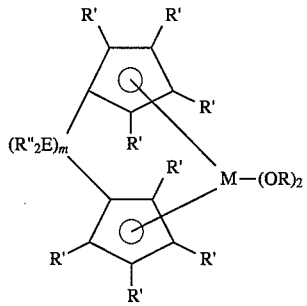 (Ib)

wherein:
R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;
R" independently each occurrence is hydrogen or a group selected from silyl, hydrocarbyl and combinations thereof, said R" having up to 30 carbon or silicon atoms;
m is 1 to 8; and
M and R are as previously defined; and
wherein the metal compound of the formula: $M(OR)_4$ is contacted with a dianionic salt compound corresponding to the formula:

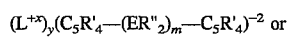 or

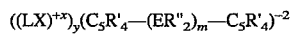

wherein L, R', E, R", X, m, x, and y are as previously defined.

Exemplary metal complexes of bridged bis-cyclopentadienyl metal dihydrocarbyloxy coordination complexes include those complexes of formula (Ib) wherein E is silicon or carbon, R" independently each occurrence is hydrogen or a group selected from silyl, hydrocarbyl and combinations thereof, said R" having up to 30 carbon or silicon atoms, and m is 1 to 8. Preferably R" independently each occurrence is methyl, benzyl, tert-butyl, or phenyl.

Such bridged bis(cyclopentadienyl) structures are especially suited for use as catalyst, or precursors thereof, for the preparation of polymers having stereoregular molecular structure. In such capacity it is preferred that the complex be nonsymmetrical or possess a chiral, stereorigid structure. Examples of the first type are compounds possessing different delocalized n-bonded systems, such as one cyclopentadienyl group and one indenyl group. Examples of chiral structures include bis-indenyl complexes.

Exemplary bridged bis(cyclopentadienyl) metal dihydrocarbyloxy complexes of formula (Ib) are those wherein the bridged ligand group is: dimethylsilyl-bis-cyclopentadienyl, dimethylsilyl-bis-tetramethylcyclopentadienyl, dimethylsilyl-bis-indenyl, isopropylidene-cyclopentadienyl-fluorenyl, 2,2'-biphenyldiylbis(3,4-dimethyl-1-cyclopentadienyl), and 6,6-dimethyl-2,2'-biphenylbis(3,4-dimethyl-1-cyclopentadienyl).

In a preferred embodiment, the moiety $((LX)^{+x})_y$ in the dianionic salt compound corresponds to $((MgCl)^+)_2$. Use of such a dianionic salt compound in the present process gives as a byproduct MgCl(OR) which can be easily separated from the desired product.

The molar ratio of the dianionic salt compound to the metal dihydrocarbyloxy compound $M(OR)_4$ can vary between wide limits. Although an improved process can be obtained with dianionic salt compound to metal compound molar ratios of 0.5:1 and higher, for example, up to 10:1, or preferably up to 5:1, the yield of the process and the purity of the desired products are high at ratios of 1:1 and slightly higher, for example, up to 1.5:1, preferably up to 1.2:1.

In the present process an aprotic organic diluent is used. Suitable examples of such diluents are ethers and hydrocarbons. Preferably the hydrocarbon solvent is an aliphatic or cycloaliphatic hydrocarbon solvent having from 5 to 10 carbon atoms. Suitable solvents are pentane, hexane, heptane, Isopar E (a mixture of isoparaffinic hydrocarbons available from Exxon Chemical Inc.), isooctane, cyclohexane, and methylcyclohexane.

Carrying out the reaction in a hydrocarbon solvent has the advantage that the product dihydrocarbyloxy complexes of formulas (I), (Ia), and (Ib) are soluble, whereas the byproduct L-R or LX-R generally is not. The desired products thus can be easily recovered, if desired, by filtration or other liquid-solid separation methods. By subjecting the liquid thus obtained to a stripping step to strip off the volatile solvent a highly pure product is obtained.

The temperature at which the process is conducted is not critical, but is preferably below the boiling point of the diluent. Preferred temperatures range from 0° C. to 100° C., more preferably from 10° C. to 80° C., and most preferably from 20° to 60° C.

Generally the reactants are contacted under an inert atmosphere for a time from several minutes to several days. The presence of oxygen and moisture are preferably avoided. The reactants can be added in any order. Agitation may be employed if desired.

According to a further aspect the present invention provides a process for preparing bridged mono-or biscyclopentadienyl dihydrocarbyl metal coordination complexes of formulas (II), (IIa), and (IIb) by contacting a corresponding metal dihydrocarbyloxy coordination complex of formula (I), (Ia), or (Ib) obtainable as described hereinbefore with a hydrocarbylation agent comprising a Group 1, 2, 12 or 13 metal or metal derivative and at least one hydrocarbyl group R''', to form the dihydrocarbyl metal coordination complex of formula (II), (IIa) or (IIb).

Surprisingly, it has been found that the dihydrocarbyloxy complexes of formulas (I), (Ia), and (Ib) are stable compounds which can readily be converted to the corresponding dihydrocarbyl compounds of formulas (II), (IIa), or (IIb) in high yields and purity. The present hydrocarbylation process, especially in combination with the process for preparing the metal dihydrocarbyloxy coordination complexes of formulas (I), (Ia), or (Ib) as described herein before, enables the valuable complexes of formulas (II), (IIa), or (IIb) to be prepared in high overall yields compared to a process starting from metal tetrahalide compounds.

In a preferred embodiment, a metal dihydrocarbyl coordination complex corresponding to the formula:

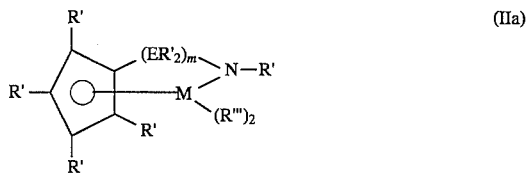
(IIa)

wherein R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;

m is 1 or 2; and

M and R''' are as previously defined;

is prepared by contacting a metal dihydrocarbyloxy coordination complex corresponding to the formula:

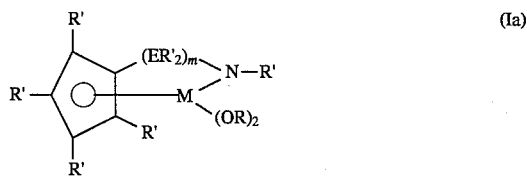
(Ia)

wherein: M, R', E, R, and m are as previously defined;
with the hydrocarbylation agent.

In another preferred embodiment, a metal dihydrocarbyl coordination complex corresponding to the formula:

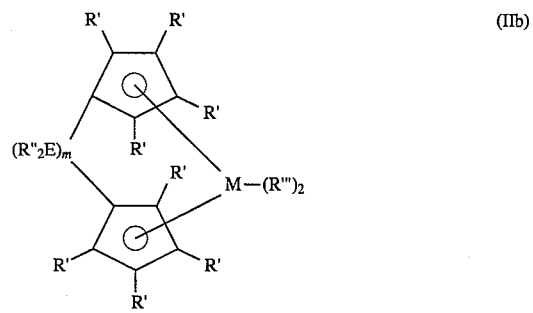
(IIb)

wherein:
R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon-or carbon;

R'' independently each occurrence is hydrogen or a group selected from silyl, hydrocarbyl and combinations thereof, said R'' having up to 30 carbon or silicon atoms;

m is 1 to 8; and

M and R''' are as previously defined;

is prepared by contacting a metal dihydrocarbyloxy coordination complex corresponding to the formula:

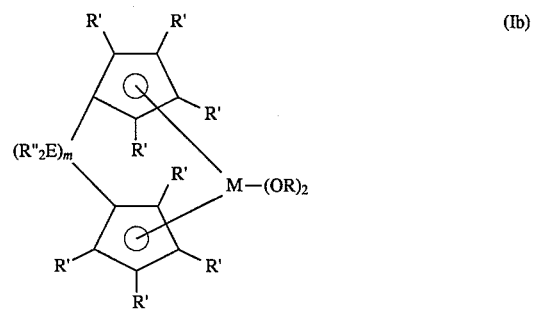
(Ib)

wherein R', E, R'', M, R, and m are as previously defined;
with the hydrocarbylation agent.

In a further preferred embodiment, the metal dihydrocarbyloxy coordination complex of formula (I), (Ia), or (Ib), used as starting compound in the preparation of complexes of formulas (II), (IIa) or (IIb), is prepared by contacting in the presence of an aprotic organic diluent a metal compound of the formula: M(OR)$_4$ wherein M and R are as previously defined with a dianionic salt compound corresponding to the formula:

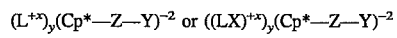

wherein:
L is a metal of Group 1 or 2 of the Periodic Table of the Elements,

X independently is chloro, bromo, or iodo, x and y are either 1 or 2 and the product of x and y equals 2, and Cp*, Z, and Y are as previously defined;

optionally followed by recovering the complex corresponding to formula (I).

In the complexes of formulas (I), (Ia), and (Ib), M is titanium, and R independently each occurrence is a hydrocarbyl group having from 1 to 20 carbon atoms, preferably R each occurrence is independently selected from the group consisting of alkyl, aryl, aralkyl, and alkaryl groups, more preferably alkyl groups having from 2 to 6 carbon atoms and aryl, aralkyl, and alkaryl groups having from 6–10 carbon atoms, and most preferably R each occurrence is independently selected from the group consisting of isopropyl, n-butyl, and t-butyl.

Preferred embodiments of the present process to prepare the complexes of formulas (I), (Ia), and (Ib) are illustrated hereinbefore and hereby incorporated by reference.

The complexes of formulas (I), (Ia), and (Ib) as obtained can be recovered or purified, if desired, prior to proceeding with the hydrocarbylation step.

The hydrocarbyl group R''' in formulas (II), (IIa), and (IIb) and present in the hydrocarbylation agent generally has from 1 to 20 carbon atoms and can be an aliphatic, cycloaliphatic, or aromatic hydrocarbon or a mixture thereof. Preferably, R''' is selected from the group consisting of alkyl, aryl and aralkyl groups, more preferably from alkyl groups having from 1 to 6 carbon atoms, or aralkyl groups having from 7 to 10 carbon atoms. Most preferably R''' is methyl, neopentyl, or benzyl.

The hydrocarbylation agent comprises a Group 1, 2, 12 or 13 metal or metal derivative and at least one hydrocarbyl group R'''. Suitable examples of the hydrocarbylation agent include LiR''', MgR'''$_2$, MgR''' X (wherein X is halogen, preferably chloro), AlR'''$_3$, and R'''-substituted aluminoxane. Suitable R'''-substituted aluminoxanes preferably include $C_{1-6}$-alkylaluminoxanes, especially methylaluminoxane. Alkylaluminoxanes are well known in the art and methods for their preparation are illustrated by U.S. Pat. Nos. 4,592,199; 4,544,762; 5,015,749 and 5,041,585. Preferably, the hydrocarbylation agent comprises LiR''' or AlR'''$_3$. More preferably the hydrocarbylation agent is trialkyl aluminum, most preferably trimethyl aluminum.

Specific highly preferred complexes of formula (IIa) include: (tert-butylamido)(tetramethyl-$\eta^5$-cyclopentadienyl)-1,2-ethanediyltitanium dimethyl, (tert-butylamido)(tetramethyl-$\eta^5$-cyclopentadienyl)-1,2-ethanediyltitanium dibenzyl, (tert-butylamido)(tetramethyl-$\eta^5$-cyclopentadienyl)dimethylsilanetitanium dimethyl, (tert-butylamido)(tetramethyl-$\eta^5$-cyclopentadienyl)dimethylsilanetitanium dibenzyl, (methylamido)(tetramethyl-$\eta^5$-cyclopentadienyl)dimethylsilanetitanium dimethyl, (methylamido)(tetramethyl-$\eta^5$-cyclopentadienyl)dimethylsilanetitanium dibenzyl, (phenylamido)(tetramethyl-$\eta^5$-cyclopentadienyl)dimethylsilanetitanium dimethyl, (phenylamido)(tetramethyl-$\eta^5$-cyclopentadienyl)dimethylsilanetitanium dibenzyl, (benzylamido)(tetramethyl-$\eta^5$-cyclopentadienyl)dimethylsilanetitanium dimethyl, (benzylamido)(tetramethyl-$\eta^5$cyclopentadienyl)dimethylsilanetitanium dibenzyl, (tertbutylamido)($\eta^5$-cyclopentadienyl)-1,2-ethanediyltitanium dimethyl, (tert-butylamido)($\eta^5$-cyclopentadienyl)-1,2ethanediyltitanium dibenzyl, (tert-butylamido)($\eta^5$-cyclopentadienyl)dimethylsilanetitanium dimethyl, (tertbutylamido)($\eta^5$-cyclopentadienyl)dimethylsilanetitanium dibenzyl, (methylamido)($\eta^5$-cyclopentadienyl)dimethylsilanetitanium dimethyl, (t-butylamido)($\eta^5$-cyclopentadienyl)dimethylsilanetitanium dibenzyl, (t-butylamido)indenyldimethylsilanetitanium dimethyl, (t-butylamido)indenyldimethylsilanetitanium dibenzyl, and (benzylamido)indenyldimethylsilanetitanium dibenzyl.

The molar ratio of the hydrocarbylation agent to the complex of formulas ( I ), ( Ia), and ( Ib ) can vary between wide limits, but is preferably between 0.1:1 and 20:1, more preferably between 0.5:1 to 10:1. Advantageously, an equivalent amount or a slight excess of R'''-groups in the hydrocarbylation agent is used with respect to the metal hydrocarbyloxy compound of formulas (I), (Ia), or (Ib), i.e., a ratio of from 2.0:1 to 4.0:1, more preferably of from 2.1:1 to 3:1.

The temperature at which the hydrocarbylation step is conducted is not critical, but is preferably below the boiling point of the aprotic organic diluent Preferred temperatures range from 0° C. to 100° C., more preferably from 10° C. to 80° C.

Generally the reactants are contacted under an inert atmosphere for a time from several minutes to several days. The reactants can be added in any order. Agitation may be employed if desired.

In the present hydrocarbylation step an aprotic organic diluent is used. Preferably, diluents are used in which the complexes of formulas (I), (Ia), and (Ib) are readily soluble, optionally upon heating. Suitable examples of such solvents are ethers and hydrocarbons. Preferably the solvent is a hydrocarbon, advantageously an aliphatic or cycloaliphatic hydrocarbon solvent having from 5 to 10 carbon atoms. Suitable solvents are pentane, hexane, heptane, Isopar E, isooctane, cyclohexane, and methylcyclohexane.

Carrying out the reaction in a hydrocarbon solvent has the advantage that the product hydrocarbyl complexes of formulas (II), (IIa), and (IIb) are soluble, whereas the byproduct Group 1, 2, 12 or 13 metal or metal derivative hydrocarbyloxides are generally not. So are the byproducts LiOR and Mg(OR)X generally not soluble in hydrocarbons. The desired products thus can be easily separated from these insoluble byproducts, if desired, by filtration or other liquid-solid separation methods. By subjecting the liquid thus obtained to a stripping step to strip off the volatile solvent a highly pure product is obtained. When trimethylaluminum is used as hydrocarbylation agent the byproduct formed comprises a methylaluminum dihydrocarbyloxyde, which is volatile. This byproduct can be removed from the desired product by applying a vacuum so as to remove both the byproduct and the solvent/diluent in one step.

According to another aspect the present invention provides a process for preparing bridged mono-or bis(cyclopentadienyl) metal dihalide coordination complexes of formulas (III), (IIIa) or (IIIb) by contacting a corresponding metal dihydrocarbyloxy coordination complex of formula (I), (In), or (Ib) obtainable as described hereinbefore, with a halogenation agent comprising a Group 13 or 14 element or derivative thereof and at least one halo group X, to form the metal dihalide coordination complex of formulas (III), (IIIa) or (IIIb).

Surprisingly, it has been found that the dihydrocarbyloxy complexes of formulas (I), (In) or (b) are stable compounds which can easily be converted to the corresponding dihalide compounds of formulas (III), (IIIa) or (IIIb) in high yields and purity. The present halogenation process, especially in combination with the process for preparing the metal dihydrocarbyloxy coordination complexes of formulas (I), (In) or (lb) as described herein before, enables the complexes of formulas (III), (IIIa) or (IIIb) to be prepared in high yields compared to a process starting from metal tetrahalide compounds.

In a preferred embodiment, a metal dihalide coordination complex corresponding to the formula (IIIa):

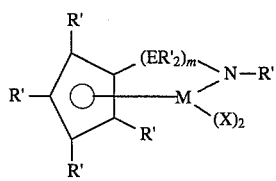

(IIIa)

wherein R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;

m is 1 or 2; and

M and X are as previously defined;

is prepared by contacting a metal dihydrocarbyloxy coordination complex corresponding to the formula:

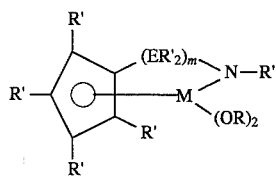

(Ia)

wherein: M, R', E, R, and m are as previously defined; with the halogenation agent.

In another preferred embodiment, a metal dihalide coordination complex corresponding to formula (IIIb)

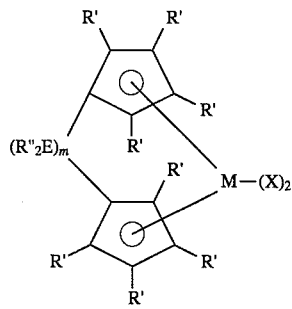

(IIIb)

wherein:

R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;

R" independently each occurrence is hydrogen or a group selected from silyl, hydrocarbyl and combinations thereof, said R" having up to 30 carbon or silicon atoms;

m is 1 to 8; and

M and X are as previously defined;

is prepared by contacting a metal dihydrocarbyloxy coordination complex corresponding to the formula:

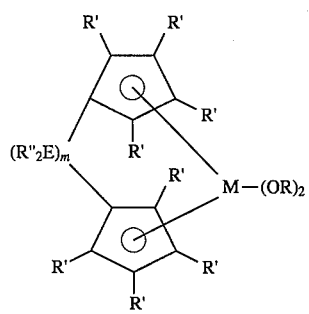

(Ib)

wherein R', E, R", M, R, and m are as previously defined; with the halogenation agent.

In a further preferred embodiment, the metal dihydrocarbyloxy coordination complex of formulas (I), (Ia) or (Ib), used as starting compound in the preA process according to claim 1 wherein the dianionic salt compound corresponds to the formula: ( $(MgCl^+)_2(Cp^*-Z-Y)^{-2}$ wherein $Cp^*$, Z, and Y are as defined in claim 1. paration of complexes of formulas (III), (IIIa) or (IIIb), is prepared by contacting in the presence of an aprotic organic diluent a metal compound of the formula: $M(OR)_4$ wherein M and R are as previously defined with a dianionic salt compound corresponding to the formula:

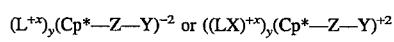

$(L^{+x})_y(Cp^*-Z-Y)^{-2}$ or $((LX)^{+x})_y(Cp^*-Z-Y)^{+2}$ wherein:

L is a metal of Group 1 or 2 of the Periodic Table of the Elements,

X independently is chloro, bromo, or iodo, x and y are either 1 or 2 and the product of x and y equals 2, and $Cp^*$, Z, and Y are as previously defined;

optionally followed by recovering the complex corresponding to formula (I).

In the complexes of formulas (I), (Ia), and (Ib), M is titanium, and R independently each occurrence is a hydrocarbyl group having from 1 to 20 carbon atoms, preferably R each occurrence is independently selected from the group consisting of alkyl, aryl, aralkyl, and alkaryl groups, more preferably alkyl groups having from 2 to 6 carbon atoms and aryl, aralkyl, and alkaryl groups having from 6–10 carbon atoms, and most preferably R each occurrence is independently selected from the group consisting of isopropyl, n-butyl, and t-butyl.

Preferred embodiments of the present process to prepare the complexes of formulas (I), (Ia), and (Ib) are illustrated hereinbefore and hereby incorporated by reference.

The complexes of formulas (I), (Ia), and (Ib) as obtained can be recovered or purified, if desired, before proceeding with the halogenation process.

The halo group X in formulas (III), (IIIa), and (IIIb) and in the halogenation agent can be chloro, or iodo, but is preferably chloro, bromo, The halogenation agent comprises a Group 13 or 14 element or derivative thereof and at least one halo group X. Suitable examples of the halogenation agent include the halides, preferably chlorides, of boron, aluminum and silicon. Preferably, the halogenation agent is selected from the group consisting of silicon tetrachloride, boron trichloride, and alkylaluminum chlorides, more preferably dialkylaluminum chlorides such as diethylaluminum chloride. Most preferred halogenation agents are silicon tetrachloride and boron trichloride.

Specific highly preferred complexes of formula IIIb include: (tert-butylamido)(tetramethyl-$\eta^5$-cyclopentadienyl)-1,2-ethanediyltitanium dichloride, (tert-butylamido)(tetramethyl-η⁵-cyclopentadienyl)dimethylsilanetitanium dichloride, (methylamido)(tetramethyl-η⁵-cyclopentadienyl)dimethylsilanetitanium dichloride, (phenylamido)(tetramethyl-η⁵-cyclopentadienyl)dimethylsilanetitanium dichloride, (benzylamido)(tetramethyl-η⁵-cyclopentadienyl)dimethylsilanetitanium dichloride, (tert-butylamido)(η⁵-cyclopentadienyl)-1,2-ethanediyltitanium dichloride, (tert-butylamido)(η⁵-cyclopentadienyl)dimethylsilanetitanium dichloride, (methylamido)(η⁵cyclopentadienyl)dimethylsilanetium dichloride, and (t-butylamido)indenyldimethylsilanetitanium dichloride.

The molar ratio of the halogenation agent to the complex of formulas (I), (Ia), and (Ib) can vary between wide limits, but is preferably between 0.1:1 and 20:1, more preferably between 0.5:1 to 10:1. Advantageously, an equivalent amount or slight stoichiometric excess of halogenation agent is used with respect to the metal dihydrocarbyloxy compound of formula (I), (Ia) or (Ib), i.e. a ratio of 2.0:1 to 4.0:1, more preferably of from 2.1:1 to 3:1.

The temperature at which the halogenation step is conducted is not critical, but is preferably below the boiling point of the diluent. Preferred temperatures range from 0° C. to 100° C., more preferably from 10° C. to 80° C.

Generally the reactants are contacted under an inert atmosphere for a time from several minutes to several days. The reactants can be added in any order. Agitation may be employed if desired.

In the present halogenation step an aprotic organic diluent is used. Preferably, diluents are used in which the complexes of formulas (I), (Ia), and (Ib) are readily soluble, optionally upon heating. Suitable examples of such solvents are ethers and hydrocarbons. Preferably the solvent is a hydrocarbon, advantageously an aliphatic or cycloaliphatic hydrocarbon solvent having from 5 to 10 carbon atoms. Suitable solvents are pentane, hexane, heptane, Isopar E, isooctane, cyclohexane, and methylcyclohexane.

In general, isolation of the desired complexes can take place as required by the byproducts. Removal of volatiles, such as the solvent, is preferably carried out by vacuum distillation at elevated temperatures. For example, when silicon tetrachloride is used as halogenation agent the byproduct formed comprises a hydrocarbyloxy silicon chloride, which is volatile. This byproduct can be easily removed from the desired product by using vacuum distillation. Highly pure products are generally obtained, as compared to the prior art methods which require extensive filtration and recrystallization steps.

The compounds prepared with the processes according to the present invention, that is the complexes of formulas (I), (Ia), (Ib), (II), (IIa), (IIb), (III), (IIIa) and (IIIb) can be used as components of catalyst systems, or precursors therefor, useful in addition polymerization processes.

In a process for preparing a polymer of one or more addition polymerizable monomers, a catalyst comprising a metal coordination complex of any of the above-mentioned formulas and an activating cocatalyst are contacted with one or more addition polymerizable monomers under addition polymerization conditions. Suitable activating cocatalysts are described in U.S. patent application Nos. 545,403, filed Jul. 3, 1990 (corresponding to EP-A-0,416,815) and 817,202, filed Jan. 6, 1992 (corresponding to WO-A-92/10360), which are incorporated herein by reference.

"Addition polymerizable monomers" include for example ethylenically unsaturated monomers, conjugated or nonconjugated dienes, polyenes, etc. Preferred monomers include the $C_{2-10}$ α-olefins especially ethylene, propylene, isobutylene, 1-butene, 1-hexene, 4-methyl-1-pentene, and 1-octene. Other preferred monomers include styrene, halo-or alkyl substituted styrene, vinyl benzocyclobutane, 1,4-hexadiene, ethylidenenorbornene, cyclopentene, and norbornene.

Suitable catalysts for use according to the present invention are prepared by combining the metal coordination complex of formulas (I), (II), or (III) and activating cocatalyst compound in any order and in any suitable manner. Preferably the ratio of the coordination complex and cocatalyst on a molar basis is from about 1:0.1 to about 1:10,000. It will, of course, be appreciated that the catalyst system may also be formed insitu if the components thereof are added directly to the polymerization process and a suitable solvent or diluent, including condensed monomer, is used in said polymerization process. Suitable solvents include toluene, ethylbenzene, alkanes and mixtures thereof. In certain cases the catalysts may be isolated from solution and retained under inert atmosphere prior to use. The catalysts' components are sensitive to both moisture and oxygen and should be handled and transferred in an inert atmosphere such as nitrogen, argon or helium or under vacuum.

The polymerization is conducted according to known techniques for Ziegler-Natta or Kaminsky-Sinn type polymerizations. That is, the monomer(s) and catalyst are contacted at a temperature from −30° C. to 250° C., at reduced, elevated or atmospheric pressures. The polymerization is conducted under an inert atmosphere which may be a blanketing gas such as nitrogen, argon, hydrogen, ethylene, etc. or under vacuum. Hydrogen may additionally be utilized in the control of molecular weight through chain termination as is previously known in the art. The catalyst may be used as is or supported on a suitable support such as alumina, $MgCl_2$ or silica to provide a heterogeneous supported catalyst. A solvent may be employed if desired. Suitable solvents include toluene, ethylbenzene, alkanes and excess vinyl aromatic or olefin monomer. The reaction may also be conducted under solution or slurry conditions, in a suspension utilizing a perfluorinated hydrocarbon or similar liquid, in the gas phase, i.e. utilizing a fluidized bed reactor, or in a solid phase powder polymerization. A catalytically effective amount of the present catalyst and cocatalyst are any amounts that successfully result in formation of polymer. Such amounts may be readily determined by the routine experimentation by the skilled artisan. Preferred amounts of catalyst and cocatalyst are sufficient to provide an equivalent ratio of addition polymerizable monomer:catalyst of from $1 \times 10^{10}:1$ to 100:1, preferably from $1 \times 10^{8}:1$ to 500:1, most preferably $1 \times 10^{6}:1$ to 1000:1. The cocatalyst is generally utilized in an amount to provide an equivalent ratio of cocatalyst:catalyst from 10,000:1 to 0.1:1, preferably from 1,000:1 to 1:1.

It is to be understood that the metal complex may undergo various transformations or form intermediate species prior to and during the course of a polymerization. Thus other precursors could possibly be conceived to achieve the same catalytic species as are herein envisioned without departing from the scope of the present invention.

The resulting polymeric product is recovered by filtering or other suitable technique. Additives and adjuvants may be incorporated in the polymers of the present invention in order to provide desirable characteristics. Suitable additives include pigments, UV stabilizers, antioxidants, blowing agents, lubricants, plasticizers, photosensitizers, and mixtures thereof.

Having described the invention, the following examples are provided to further illustrate the same and are not to be construed as limiting.

Example 1

Preparation of (Tert-butylamido)dimethyl(tetramethyl-$\eta^5$-cyclopentadienyl)silane titanium diisopropoxide In a drybox, 24.95 g of titaniumtetraisopropoxide (Ti(O-$^i$Pr)$_4$) (Aldrich Chemical Company) (88 mmol) is dissolved in about 200 ml of hexane. 58 g of solid di(chloromagnesium) (tert-butylamido)-dimethyl(tetramethylcyclopentadienyl)silane complexed with dimethoxyethane, [Me$_4$C$_5$SiMe$_2$N$^t$Bu][MgCl]$_2$(DME)$_n$ (effective molecular weight by titration: about 629 g/mole; 92 mmol) (prepared according to the following procedure: In an apparatus consisting of a 3l round bottom flask which was equipped with a stirrer, a condenser, and a nitrogen inlet was loaded 500 ml of toluene, followed by 106 g of Me$_4$C$_5$HSiMe$_2$NH$^t$Bu, and then 380 ml of 2.2 M $^i$PrMgCl in Et$_2$O. The mixture was then heated, and the ether removed by distillation and trapped in a condenser cooled to −78° C. After five hours of heating, the heater was turned off, and 450 ml of dimethoxyethane (DME) was slowly added to the hot, stirred solution, resulting in the precipitation of a white solid. The solution was allowed to cool to room temperature, the solid was allowed to settle, and the supernatant was decanted from the solid. The solid was resuspended in Isopar E and filtered. 210 g (79 percent yield) [Me$_4$C$_5$SiMe$_2$N$^t$Bu][MgCl]$_2$(DME)n was obtained as off-white solid.) is added to the flask, using about 50 ml of additional hexane. The mixture is stirred overnight at room temperature, then filtered through a medium porosity fritted glass filter (10–15 μm porosity). The solids remaining on the frit are washed with additional hexane until the washings are colorless. A yellow/orange solution is obtained, and the volatile materials are removed from this solution under reduced pressure to leave (Me$_4$C$_5$SiMe$_2$N$^t$Bu)Ti(O$^i$Pr)$_2$ as a yellow crystalline solid in essentially quantitative yield. $^1$H NMR (C$_6$D$_6$): 4.57 ppm (septet, 2H), 2.16 ppm (s, 6H), 1.91 ppm (s, 6H), 1.37 ppm (s, 9H), 1.15 ppm (d, 12H), and 0.65 ppm (6H).

Example 2

Preparation of (Tert-butylamido)dimethyl(tetramethyl-$\eta^5$-cyclopentadienyl)silane titanium dichloride In a drybox, 5.0 g of (Me$_4$C$_5$SiMe$_2$N$^t$Bu)Ti(O$^i$Pr)$_2$ (12.0 mmol) is dissolved in about 50 ml of hexane. Silicon tetrachloride (Aldrich, 99,999%, 2.9 ml, 25.3 mMol) is added by syringe. The color immediately darkens and a precipitate begins to form. The reaction mixture is stirred overnight (about 18 hours). At the end of this time, the volatile materials are removed under reduced pressure to leave (Me$_4$C$_5$SiMeN$^t$Bu)TiCl$_2$ as a yellow solid (4.35 g, 98% yield). The material is identified by comparison of its $^1$H NMR spectrum with spectra of the complex made by other routes. 1H NMR (C$_6$D$_6$): 2.00 ppm (s, 6H), 1.99 ppm (s, 6H), 1.42 ppm (s, 9H), 0.42 ppm (s, 6H).

Example 3

Preparation of (Tert-butylamido)dimethyl(tetramethyl-$\eta^5$-cyclopentadienyl)silane titanium dimethyl In a drybox, 0.26 g of (Me$_4$C$_5$SiMe$_2$N$^t$Bu)Ti(O$^i$Pr)$_2$ (0.63 mMol) is dissolved in about 15 mL of hexane. Trimethylaluminum (Aldrich, 2M in hexane, 0.95 ml, 1.9 mmol) is added by syringe. The solution is heated to gentle reflux. After overnight (about 18 hours) reflux, the solution turned brown. The volatile materials are then removed under reduced pressure to leave (Me$_4$C$_5$SiMe$_2$N$^t$Bu)TiMe$_2$ as a pale brown solid. The material is identified by comparison of its 1H NMR spectrum with spectra of the complex made by other routes. $^1$H NMR (C$_6$D$_6$): 1.96 ppm (s, 6H)), 1.85 ppm (s, 6H) 1.56 ppm (s, 9H), 0.15 (s, 6H), 0.43 ppm (s, 6H).

What is claimed is:

1. A process for preparing a metal dihydrocarbyloxy coordination complex corresponding to the formula:

$$Cp^* - M \begin{matrix} Z - Y \\ \\ (OR)_2 \end{matrix} \quad (I)$$

wherein:

M is titanium;

Cp* is a cyclopentadienyl group bound in an $\eta^5$ bonding mode to M or such a cyclopentadienyl group substituted with from one to four substituents selected from the group consisting of hydrocarbyl, silyl, germyl, halo, hydrocarbyloxy, amino, and mixtures thereof, said substituent having up to 20 nonhydrogen atoms, or optionally, two substituents together cause Cp* to have a fused ring structure;

Z is a divalent moiety comprising boron, or a member of Group 14 of the Periodic Table of the Elements, and optionally sulfur or oxygen, said moiety having up to 50 non-hydrogen atoms, and optionally Cp* and Z together form a fused ring system;

Y is a divalent anionic ligand group comprising nitrogen, phosphorus, oxygen or sulfur and having up to 20 non-hydrogen atoms, said Y being bonded to Z and M through said nitrogen, phosphorus, oxygen or sulfur, and optionally Y and Z together form a fused ring system; and R independently each occurrence is a hydrocarbyl group having from 1 to 20 carbon atoms; the steps of the process comprising:

contacting in the presence of an aprotic organic diluent a metal compound of the formula: M(OR)$_4$ wherein M and R are as previously defined with a dianionic salt compound corresponding to the formula:

$$(L^{+x})_y(Cp^*-Z-Y)^{-2} \text{ or } ((LX)^{+x})_y(Cp^*-Z-Y)^{-2}$$

wherein:

L is a metal of Group 1 or 2 of the Periodic Table of the Elements,

X independently is chloro, bromo, or iodo, x and y are either 1 or 2 and the product of x and y equals 2, and Cp*, Z, and Y are as previously defined;

to form the complex of formula (I).

2. A process according to claim 1 wherein the metal dihydrocarbyloxy coordination complex of formula (I) corresponds to the formula:

(Ia)

wherein R' each occurrence is independently selected from the group consisting of hydrogen, silyl, alkyl, aryl, germyl, cyano, halo and combinations thereof having up to 20 non-hydrogen atoms, or two R' groups together form a divalent derivative thereof;

E is silicon or carbon;

m is 1 or 2; and

M and R are as defined in claim 1; and wherein the metal compound of the formula: $M(OR)_4$ is contacted with a dianionic salt compound corresponding to the formula:

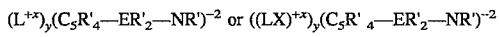

wherein L, X, x and y are as defined in claim 1, and R' and E are as defined for formula (Ia).

3. A process according to claim 1 wherein R each occurrence is independently selected from the group consisting of alkyl, aryl, aralkyl, and alkaryl groups.

4. A process according to claim 3 wherein R each occurrence is independently selected from the group consisting of alkyl groups having from 2 to 6 carbon atoms and aryl, aralkyl and alkaryl groups having from 6–10 carbon atoms.

5. A process according to claim 4 wherein R each occurrence is independently selected from the group consisting of isopropyl, n-butyl, and t-butyl.

6. A process according to claim 1 wherein the metal compound of the formula: $M(OR)_4$ is selected from the group consisting of tetra(isopropoxy)titanium, tetra(n-butoxy)titanium.

7. A process according to claim 1 wherein the dianionic salt compound corresponds to the formula: $((MgCl)^+)_2 (Cp^*-Z-Y)^{-2}$, wherein Cp*, Z, and Y are as defined in claim 1.

8. A process according to claim 1 wherein the aprotic organic diluent is a hydrocarbon or an ether.

9. A process according to claim 8 wherein the hydrocarbon is an aliphatic or cycloaliphatic hydrocarbon solvent having from 5 to 10 carbon atoms.

10. A process according to claim 1 wherein the process is conducted at a temperature between 0° C. and 100° C.

* * * * *